(12) United States Patent
Kobayashi et al.

(10) Patent No.: US 8,992,467 B2
(45) Date of Patent: Mar. 31, 2015

(54) NIPPLE COVERING MEMBER AND BREAST PUMP

(75) Inventors: Hiroshi Kobayashi, Chiba (JP); Hiroshi Kawamura, Ushiku (JP); Yukinari Awano, Hamamatsu (JP); Katsumi Mizuno, Chiba (JP); Zenichi Onuki, Kashiwa (JP); Aki Ishimaru, Kashiwa (JP)

(73) Assignee: Pigeon Corporation, Tokyo (JP)

( * ) Notice: Subject to any disclaimer, the term of this patent is extended or adjusted under 35 U.S.C. 154(b) by 359 days.

(21) Appl. No.: 12/524,696

(22) PCT Filed: Jan. 25, 2008

(86) PCT No.: PCT/JP2008/051043
§ 371 (c)(1),
(2), (4) Date: Sep. 20, 2010

(87) PCT Pub. No.: WO2008/093599
PCT Pub. Date: Aug. 7, 2008

(65) Prior Publication Data
US 2010/0130921 A1    May 27, 2010

(30) Foreign Application Priority Data
Jan. 29, 2007 (JP) ................................. 2007-018350

(51) Int. Cl.
*A61M 1/06* (2006.01)

(52) U.S. Cl.
CPC .................. *A61M 1/06* (2013.01); *A61M 1/062* (2014.02); *A61M 1/064* (2014.02)
USPC .......................................................... 604/74

(58) Field of Classification Search
CPC ....... A61M 1/06; A61M 1/062; A61M 1/066; A61M 1/068

USPC ............................... 604/313, 315, 316, 74–76
See application file for complete search history.

(56) References Cited

U.S. PATENT DOCUMENTS

| | | | |
|---|---|---|---|
| 5,100,406 A | 3/1992 | Panchula | |
| 5,885,246 A * | 3/1999 | Ford | ................................ 604/74 |

(Continued)

FOREIGN PATENT DOCUMENTS

| | | |
|---|---|---|
| CA | 2 240 268 A1 | 12/1999 |
| CH | 617 830 A5 | 6/1980 |

(Continued)

OTHER PUBLICATIONS

Machine Translation for Kobayashi et al (JP 2006-051341 A).*

(Continued)

*Primary Examiner* — Bhisma Mehta
*Assistant Examiner* — Jenna Zhang
(74) *Attorney, Agent, or Firm* — Oliff PLC

(57) ABSTRACT

A nipple coating member and a milking device for gathering mother's milk effectively. The pad of a milking device comprises a tubular frame having a large diameter side opening for inserting the nipple formed on one end side and a small diameter side opening formed on the other end side, a first flexible portion provided at a part in the circumferential direction between the large diameter side opening and the small diameter side opening of the tubular frame, and a second flexible portion provided at a position opposing the first flexible portion independently thereof. The first flexible portion can be deformed inward of the tubular frame by a pressing force from the outside of the pad, and the second flexible portion can be deformed outward of the tubular frame by a pressing force from the inside of the pad.

5 Claims, 13 Drawing Sheets

(56) References Cited

U.S. PATENT DOCUMENTS

| | | | |
|---|---|---|---|
| 5,947,923 A * | 9/1999 | Uehara et al. | 604/74 |
| 6,004,288 A * | 12/1999 | Hochstedler et al. | 604/74 |
| 6,387,072 B1 | 5/2002 | Larsson et al. | |
| 6,461,324 B1 * | 10/2002 | Schlensog | 604/74 |
| 6,579,258 B1 * | 6/2003 | Atkin et al. | 604/74 |
| 6,723,066 B2 | 4/2004 | Larsson et al. | |
| 7,396,340 B2 * | 7/2008 | Onuki et al. | 604/74 |
| 2005/0234400 A1 | 10/2005 | Onuki et al. | |
| 2005/0245860 A1 | 11/2005 | Britto et al. | |
| 2006/0106334 A1 | 5/2006 | Jordan et al. | |

FOREIGN PATENT DOCUMENTS

| | | | |
|---|---|---|---|
| JP | A-08-173507 | | 7/1996 |
| JP | A-2003-521958 | | 7/2003 |
| JP | A-2005-279044 | | 10/2005 |
| JP | 2006051341 A | * | 2/2006 |
| JP | A-2006-051341 | | 2/2006 |
| WO | WO 00/33897 | | 6/2000 |
| WO | WO 2005/042062 A1 | | 5/2005 |

OTHER PUBLICATIONS

Office Action issued in corresponding Japanese Application No. 2007-018350, mailed Aug. 24, 2010. (with English-language translation).

May 2, 2013 Office Action issued in Taiwanese Patent Application No. 097103059 (with translation).

Feb. 1, 2013 European Search Report issued in European Patent Application No. 08703870.9.

* cited by examiner

NIPPLE COVERING MEMBER AND BREAST PUMP

This application claims priority to PCT/JP2008/051043 filed Jan. 25, 2008, and Japanese Patent Application No. 2007-018350 filed Jan. 29, 2007.

BACKGROUND OF THE INVENTION

1. Technical Field

The present invention relates to a nipple covering member and breast pump for gathering breast milk from a human body.

2. Background Art

A breast pump is known that allows a nipple to enter through a large diameter side opening of a milk receiving member formed in a horn shape and that performs milking by applying negative pressure inside the milk receiving member (see, for example, Patent Reference 1: Japanese National Publication No. 2003-521958 and Patent Reference 2 : Pamphlet of International Publication No. 05/042062). A further breast pump is known which, in addition to the application of negative pressure, applies a expression load by peristaltic motion (pressing stimulations) to the nipple via the milk receiving member (see, for example, Patent Reference 3: Japanese Patent Application Laid-Open No. 2006-51341).

DISCLOSURE OF INVENTION

Problem to be Solved by the Invention

However, a nipple covering member of a conventional breast pump that utilizes pressure variations in association with negative pressure, as in Pat. Reference 1 and Patent Reference 2, is focused on application to use in milking with negative pressure, and no consideration is given to applying sufficient pressing stimulations. Further, in the breast pump of Pat. Reference 3 that applies a expression load, the nipple covering member (pad) as a whole is constituted of soft silicone rubber or the like, and this nipple covering member as a whole becomes deformed. Thus, gaps may be formed between the breast and the nipple covering member in association with the application of pressing stimulations, and there is room for improvement in this respect.

In consideration of the circumstances described above, an object of the present invention is to provide a nipple covering member and breast pump capable of gathering breast milk effectively.

Means for Solving the Problem

A nipple covering member relating to a first aspect of the present invention comprises: a tubular frame at which a large diameter side opening for inserting a nipple is formed at one end side and a small diameter side opening is formed at the other end side; a first flexible portion that is provided at a circumferential direction portion between the large diameter side opening and the small diameter side opening of the tubular frame, and that can be deformed inward of the tubular frame by a pressing force from an outside of the tubular frame; and a second flexible portion that is provided separately from the first flexible portion at a position opposing the first flexible portion between the large diameter side opening and the small diameter side opening of the tubular frame, and that can be deformed outward of the tubular frame by a pressing force from an inside of the tubular frame.

According to the above-described aspect, in, for example, a state in which a nipple has been inserted through the large diameter side opening, loads or displacements for applying stimulation to the nipple may be inputted from the outside of the first flexible portion. Accordingly, when a load (displacement) is inputted to the nipple via the first flexible portion, the second flexible portion, which is disposed at the opposite side to sandwich the nipple with the first flexible portion, suitably deforms such that a state in which the nipple or a portion of the breast in the vicinity of the nipple is in area contact is maintained. Meanwhile, portions of the present nipple covering member apart from the first and second flexible portions are constituted as the tubular frame, and thus deformations are restrained. Therefore, the present nipple covering member tracks displacements (deformations) of load input directions at the nipple (breast) and restrains deformations in other directions. Thus, with the constitution that inputs loads to particular circumferential direction locations of the nipple, the formation of gaps between the present nipple covering member and the breast is effectively suppressed.

Thus, with the nipple covering member relating to the above-described aspect, breast milk may be gathered effectively.

In the above-described aspect, the tubular frame includes a first window portion, which is formed at a circumferential direction portion between the large diameter side opening and the small diameter side opening, and a second window portion, which is formed such that skeleton portions are formed between the second window portion and two circumferential direction end portions of the first window portion, the first flexible portion is constituted with the first window portion being closed up by a elastic member, and the second flexible portion is constituted with the second window portion being closed up by a elastic member.

According to the above-described aspect, the first and second window portions formed in the tubular frame are closed off with elastic material, and the first and second flexible portions are constituted to sandwich the skeleton portions of the tubular frame. Thus, the present nipple covering member, while having a simple structure, may restrain deformations in directions in which the skeleton portions are radially displaced while allowing displacements in directions toward and away from the first and second flexible portions, which are formed non-continuously in the circumferential direction.

A breast pump relating to a second aspect of the present invention comprises: a nipple covering member relating to the first aspect; a collection vessel for collecting milk, which is connected to the small diameter side opening of the nipple covering member; stimulating device for transmitting pressing stimulations to the nipple at the first flexible portion; a nipple support portion for supporting the nipple inserted into the nipple covering member with respect to the pressing stimulations by the stimulating device on the nipple that are transmitted via the first flexible portion, the nipple support portion being disposed at the outside of the second flexible portion of the nipple covering member; and support position adjusting device capable of adjusting a support position of the nipple support portion relative to the stimulating device.

According to the above-described aspect, in the state in which a nipple has been inserted into the nipple covering member through the large diameter side opening, a position of the nipple support portion relative to the stimulating device is adjusted by the support position adjusting device as necessary, and the stimulating device is operated. Hence, pressing actions of the stimulating device are inputted to the nipple in the nipple covering member via the first flexible member as pressing loads or displacements. At these times, the nipple is supported by the nipple support portion, via the second flexible member, from the side opposite from the stimulating device. Therefore, in the present breast pump, pressing actions may be reliably transmitted to the nipple and the breast milk may be gathered effectively.

Thus, with the breast pump relating to the above-described aspect, the breast milk may be gathered effectively. Moreover, the present breast pump has a constitution in which the position of support of the nipple in the nipple covering member by the nipple support portion may be adjusted by the support position adjusting device. Therefore, suitable nipple support positions may be specified in accordance with individual differences and breast condition variations. It should be noted that the nipple support portion of the present invention may be structured integrally with the support position adjusting device.

In the above-described aspect, the breast pump may further comprise a negative pressure generating device for producing negative pressure at the inside of the nipple covering member into which the nipple has been inserted through the large diameter side opening.

According to the above-described aspect, while pressing actions are applied by the stimulating device, negative pressure is applied by the negative pressure generating device, with respect to the nipple in the nipple support member. Thus, the breast milk may be gathered even more effectively. In addition, the nipple covering member provided with the first and second flexible portions in the tubular frame restrains deformations due to negative pressure (deformations in directions other than pressing action directions). Thus, with the constitution that applies negative pressure in addition to the pressing actions, the formation of gaps between the nipple covering member and the breast is effectively suppressed.

A breast pump relating to a third aspect of the present invention comprises: a nipple covering member in which a large diameter side opening for inserting a nipple is formed at one end side and a small diameter side opening for connecting to a collection vessel for collecting milk is formed at the other end side; stimulating device that transmits pressing stimulations to the nipple at the nipple in the nipple covering member by pressing a circumferential direction portion of the nipple covering member between the large diameter side opening and the small diameter side opening; a nipple support portion for supporting the nipple inserted into the nipple covering member with respect to the pressing stimulations by the stimulating device on the nipple, the nipple support portion being disposed at an opposite side of the nipple covering member from a side at which a pressing load of the stimulating device is inputted; and support position adjusting device capable of adjusting a distance between the stimulating device and the nipple support portion.

According to the above-described aspect, in the state in which a nipple has been inserted into the nipple covering member through the large diameter side opening, a position of the nipple support portion relative to the stimulating device is adjusted by the support position adjusting device as necessary, and the stimulating device is operated. Hence, pressing actions of the stimulating device are inputted to the nipple in the nipple covering member, via the circumferential direction portion of the nipple covering member, as pressing loads or displacements. At these times, the nipple is supported by the nipple support portion from the side opposite from the stimulating device. Therefore, in the present breast pump, pressing actions may be reliably transmitted to the nipple and the breast milk may be gathered effectively.

Thus, with the breast pump relating to the above-described aspect, the breast milk may be gathered effectively. Moreover, the present breast pump has a constitution in which the position of support of the nipple in the nipple covering member by the nipple support portion may be adjusted by the support position adjusting device. Therefore, suitable nipple support positions may be specified in accordance with individual differences and breast condition variations. It should be noted that the nipple support portion of the present invention is not limited to being a structure separate from the nipple covering member and the support position adjusting device, and may be, for example, structured integrally with either one thereof.

In the above-described aspect, the nipple support portion is constituted to include a nipple support member that is constituted to be movable toward and away from the outside with respect to the nipple covering member, and the support position adjusting device is constituted to include: guiding device that guides the nipple support member so as to move toward and away from the stimulating device; and retaining device capable of retaining the nipple support member at a plurality of positions in the toward/away direction with respect to the stimulating device.

According to the above-described aspect, when an adjustment of the position of support of the nipple by the nipple support portion is being carried out, the nipple support member is moved toward or away from the stimulating device while being guided by the guiding device, and the nipple support member is retained by the retaining device at a desired position in the toward/away direction. Thus, the nipple support portion may be adjusted with ease in accordance with conditions of a user.

Effect of the Invention

A nipple covering member and breast pump relating to the present invention as described hereabove have an excellent effect in that it is possible to gather breast milk effectively.

BEST MODE FOR CARRYING OUT THE INVENTION

Figure 1:
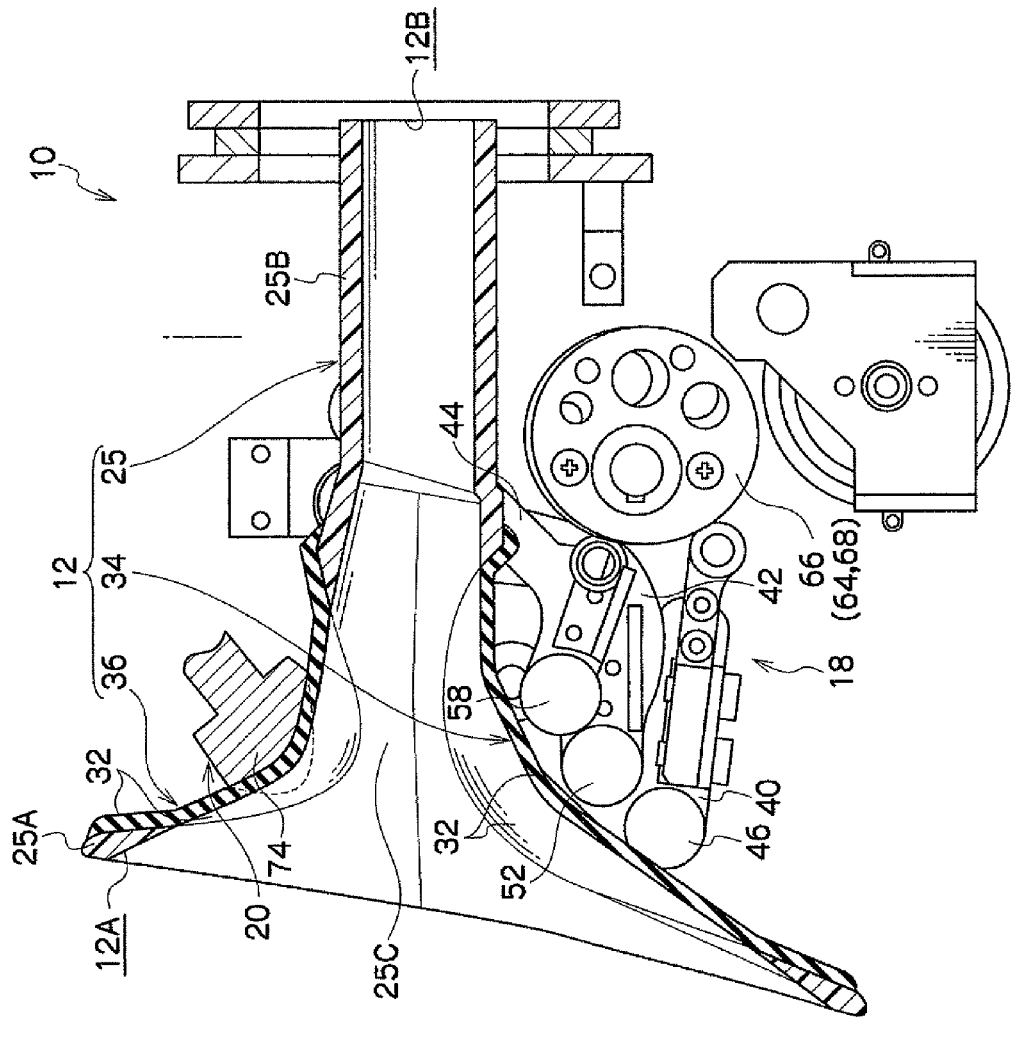
FIG. 1 is a side sectional view showing principal elements of a milking mechanism constituting a breast pump relating to an exemplary embodiment of the present invention.

A breast pump 10 which serves as a breast pump relating to an exemplary embodiment of the present invention will be described on the basis of FIG. 1 to FIG. 11. Herein, for convenience of explanation, the sides (directions) that are indicated by arrow F, arrow U and arrow L as appropriate in the drawings are a front side, an upper side and a lower side, respectively, and a direction indicated by arrow W is referred to as a width direction.

Figure 4:
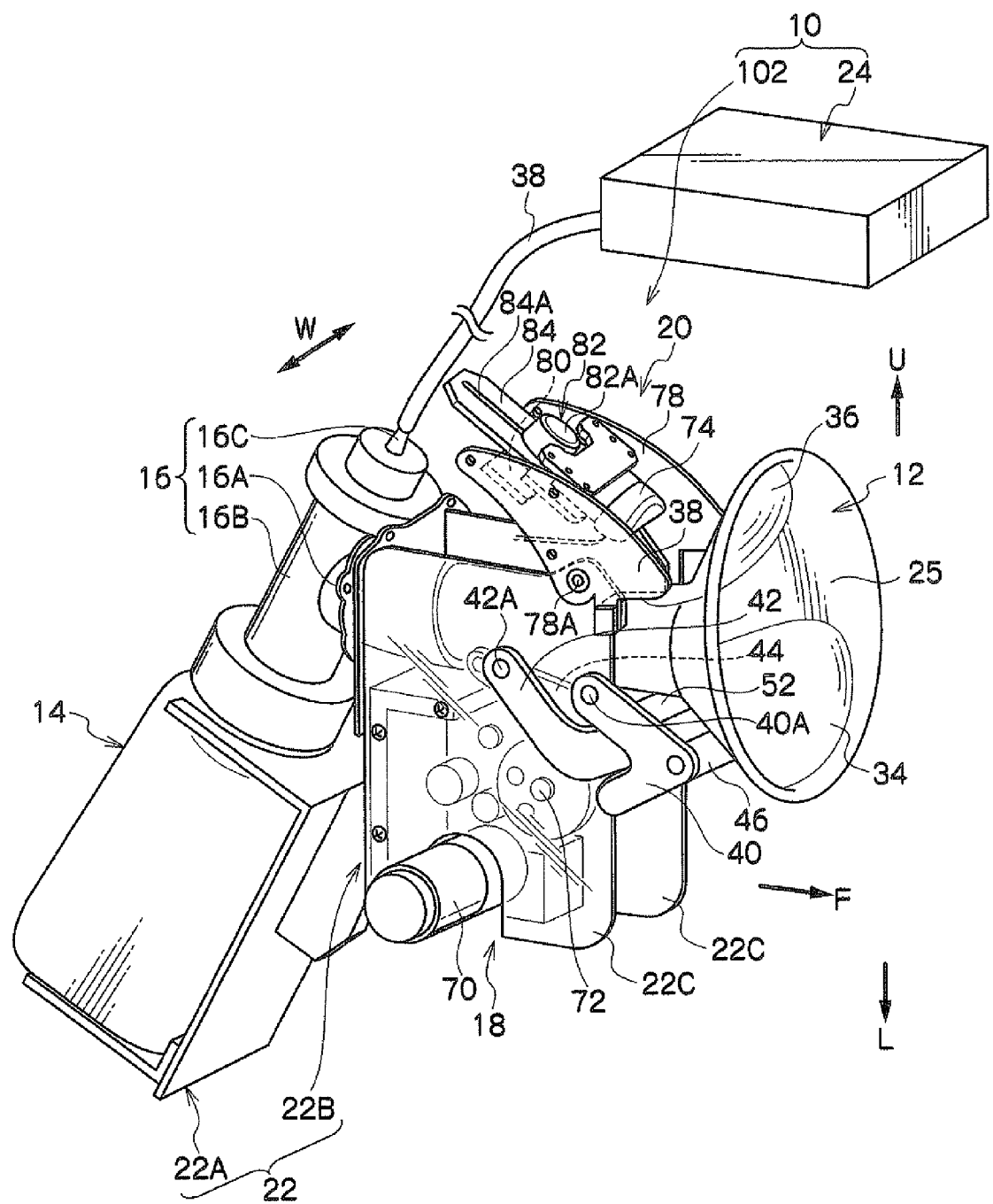
FIG. 4 is a perspective view showing general overall structure of the breast pump relating to the exemplary embodiment of the present invention.

FIG. 4 shows general overall structure of the breast pump 10 in a perspective view. As shown in this drawing, the breast pump 10 is constituted with, as principal structural elements, a pad 12 which serves as a nipple covering member that is placed on the nipple (a portion of the breast including the nipple and a vicinity of the areola) and covers the nipple from the outer peripheral side, a nursing bottle 14 which serves as a collection vessel for collecting the gathered breast milk , a connection pipe 16 which is for connecting between the pad 12 and the nursing bottle 14 to enable fluid communication, a peristalsis mechanism 18 which applies pressing stimulations to the nipple via the pad 12, a nipple support mechanism 20 which serves as a nipple support portion and a support position adjusting device that is for supporting the nipple from the side opposing the peristalsis mechanism 18, a device frame 22 which is for retaining the pad 12, the nursing bottle 14, the connection pipe 16, the peristalsis mechanism 18 and the nipple support mechanism 20 with predetermined attitudes (relative positions), and a vacuum pump unit 24 which is for applying negative pressure inside the pad 12 which is sealed up with the breast. As will be described in detail later, the peristalsis mechanism 18 applies pressing actions in directions of compressing the nipple, which serve as pressing stimulations. Herein, the peristalsis mechanism 18 is constituted to serve as a stimulating device that reproduces peristaltic motion of the tongue by an infant and implements movements so as to stroke in the opposite direction from a nearer side.

Figure 2:
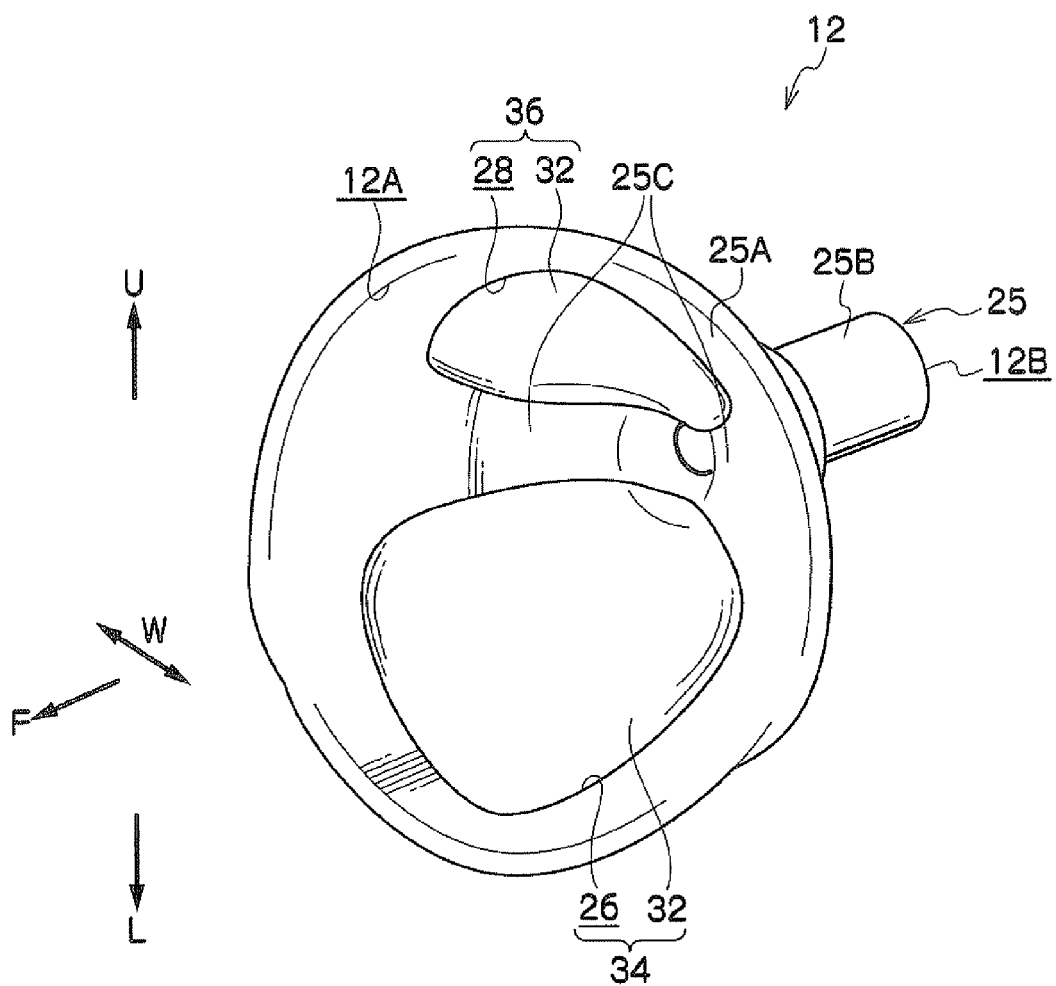
FIG. 2 is a perspective view showing a pad constituting the breast pump relating to the exemplary embodiment of the present invention.
Figure 3A:
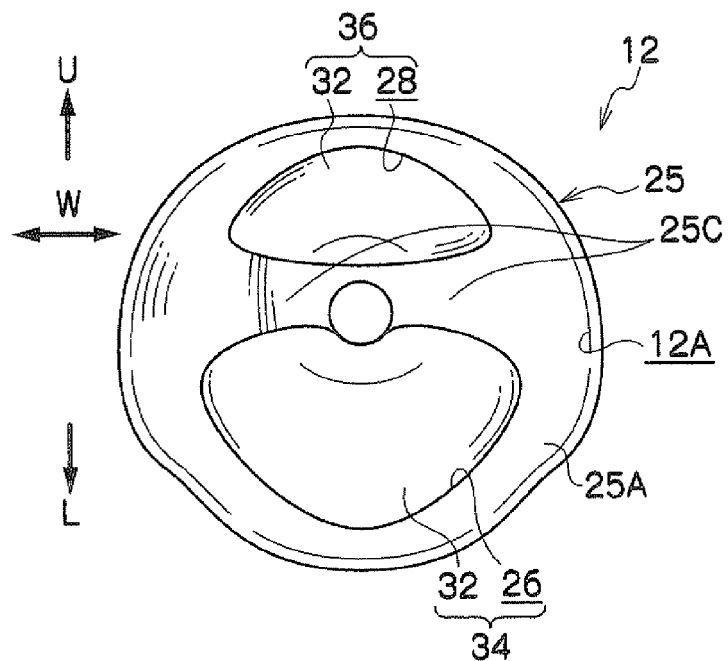
FIG. 3A is a front view showing the pad constituting the breast pump relating to the exemplary embodiment of the present invention.
Figure 3B:
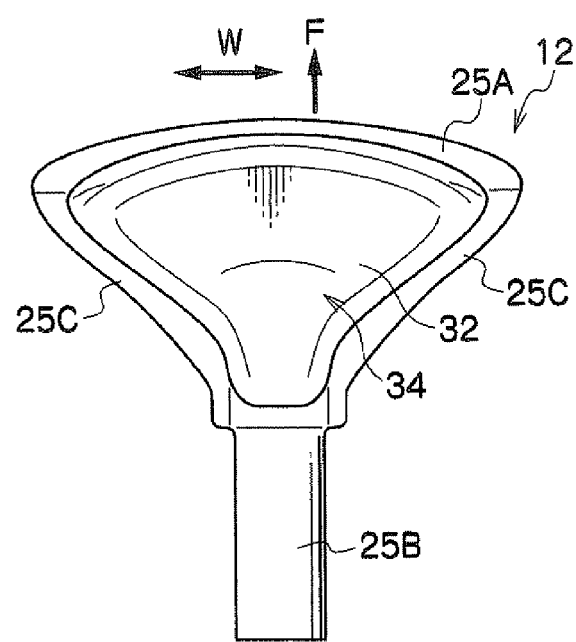
FIG. 3B is a bottom view showing the pad constituting the breast pump relating to the exemplary embodiment of the present invention.

As shown in FIG. 1 to FIG. 3, the pad 12 is formed substantially in a horn shape overall, of which a nipple entry side opening portion 12A at one end side is larger in diameter than a connection side opening portion 12B at the other end side. The pad 12 is provided with a tubular frame 25 that forms an outer shell of the pad 12 as described above. That is, the nipple entry side opening portion 12A and the connection side opening portion 12B serve as two opening ends of the tubular frame 25.

Figure 3C:
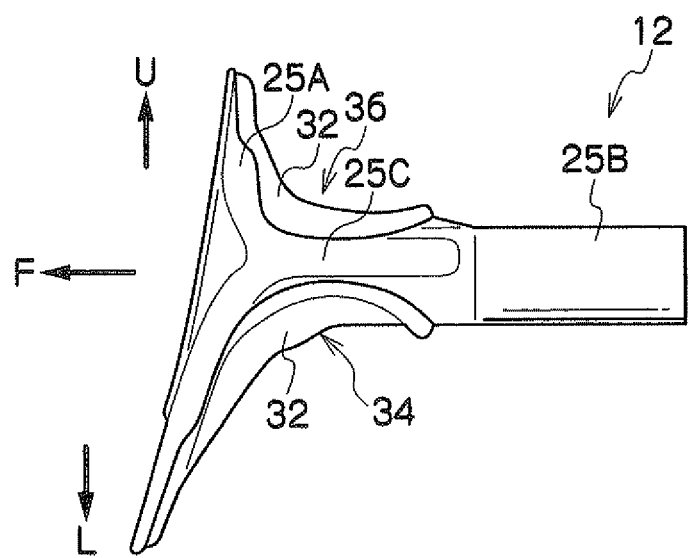
FIG. 3C is a side view showing the pad constituting the breast pump relating to the exemplary embodiment of the present invention.

As shown in FIG. 3A and FIG. 3C, the nipple entry side opening portion 12A side of the tubular frame 25 is formed as a constricting-form portion 25A with a continuously contracting diameter from the nearer side to a further side, and the connection side opening portion 12B side of the tubular frame 25 is formed as a straight pipe portion 25B which has a substantially constant diameter and connects with a minimum diameter portion of the constricting-form portion 25A. In this exemplary embodiment, the constricting-form portion 25A is formed to be vertically non-symmetrical such that a lower portion protrudes to the nearer side more and has a larger protrusion amount in the vertical direction from the straight pipe portion 25B than the upper portion.

As shown in FIG. 2 and FIG. 3A, at the lower portion of the constricting-form portion 25A of this tubular frame 25, a first window portion 26 is formed, and at an upper portion of the constricting-form portion 25A, a second window portion 28 is formed separately from the first window portion 26. The first window portion 26 and second window portion 28 each forms a substantially semicircular shape as viewed in the direction of an axis of the pad 12 (the straight pipe portion 25B). As shown in FIG. 1, the first window portion 26 and second window portion 28 are formed to reach from vicinities of the nipple entry side opening portion 12A at the nearer side to vicinities of a boundary with the straight pipe portion 25B.

As shown in FIG. 2 and FIG. 3A, skeleton portions 25C, which each extend in a substantially horizontal direction, are formed between the two ends of the first window portion 26 and the two ends of the second window portion 28 in the circumferential direction of the constricting-form portion 25A. This tubular frame 25 is integrally formed as a whole by molding. As a material structuring the tubular frame 25, as well as stiff resins such as, for example, polypropylenes, polycarbonates, polyphenylsulfones and the like, high-stiffness elastomers, silicone rubbers and the like may be used. In this exemplary embodiment, the tubular frame 25 is structured using an epoxy resin (CRYSTAL RESIN SUPER CLEAR, manufactured by NISSIN RESINS (Co., Ltd.)).

The pad 12 is provided with a first flexible portion 34 and a second flexible portion 36 which have lower stiffness than the tubular frame 25 and correspond with the first window portion 26 and the second window portion 28. The first flexible portion 34 is structured by joining peripheral edge portions of a silicone rubber 32, which is a elastic member formed as a sheet, to the tubular frame 25 at peripheral edge portions of the first window portion 26. The second flexible portion 36 is structured by joining peripheral edge portions of a silicone rubber 32, which is a elastic member formed as a sheet, to the tubular frame 25 at peripheral edge portions of the second window portion 28. In this exemplary embodiment, the silicone rubbers 32 constituting the first flexible portion 34 and the second flexible portion 36 have respective thicknesses of around 1.5 mm to 3 mm, and are capable of deforming in a flexing direction and deforming in a thickness direction. Instead of the silicone rubbers 32, the first flexible portion 34 and second flexible portion 36 may be constituted using other elastic members such as, for example, elastomers, isoprene rubbers or the like, and may be formed integrally with the tubular frame 25 by two-color molding, insert molding or the like of the flexible portions 34 and 36.

The nursing bottle 14 opens substantially upward. As shown in FIG. 4, the connection pipe 16 includes a horizontal pipe 16A that connects to the connection side opening portion 12B of the pad 12 and a standing pipe 16B that is connected with the horizontal pipe 16A, at the opposite end from the pad 12, and connects to an opening end of the nursing bottle 14 at a lower end thereof. An air escape portion 16C is provided at an upper end of the standing pipe 16B of the connection pipe 16. The air exit portion 16C is connected with the vacuum pump unit 24 via a tube 38. Preferably, a valve which allows fluid communication of breast milk while separating out air from the nursing bottle 14 may be provided at the lower end of the standing pipe 16B, and a back flow preventing device for avoiding reverse flow of the breast milk into the vacuum pump unit 24 may be formed at the upper end.

As shown in FIG. 4, the device frame 22 is structured by joining a breast milk collection side frame 22A, which principally supports the nursing bottle 14 and the connection pipe 16, with a milking side frame 22B, which principally supports (the pad 12 via) the peristalsis mechanism 18 and the nipple support mechanism 20. Although not described in detail here, the breast milk collection side frame 22A and the milking side frame 22B are constituted with a relative angle about the axis of the pad 12 being adjustable (alterable and retainable). That is, the breast pump 10 has a constitution in which, while the nursing bottle 14 is held in an attitude substantially along the vertical direction, peristaltic motion may be applied by the peristalsis mechanism 18 to various circumferential direction positions of the nipple. The above descriptions and the following descriptions are descriptions for an attitude in which the second flexible portion 36 of the pad 12 is disposed at the vertical direction upper side and the first flexible portion 34 is disposed at the lower side (the attitude shown in FIG. 4).

Figure 8:
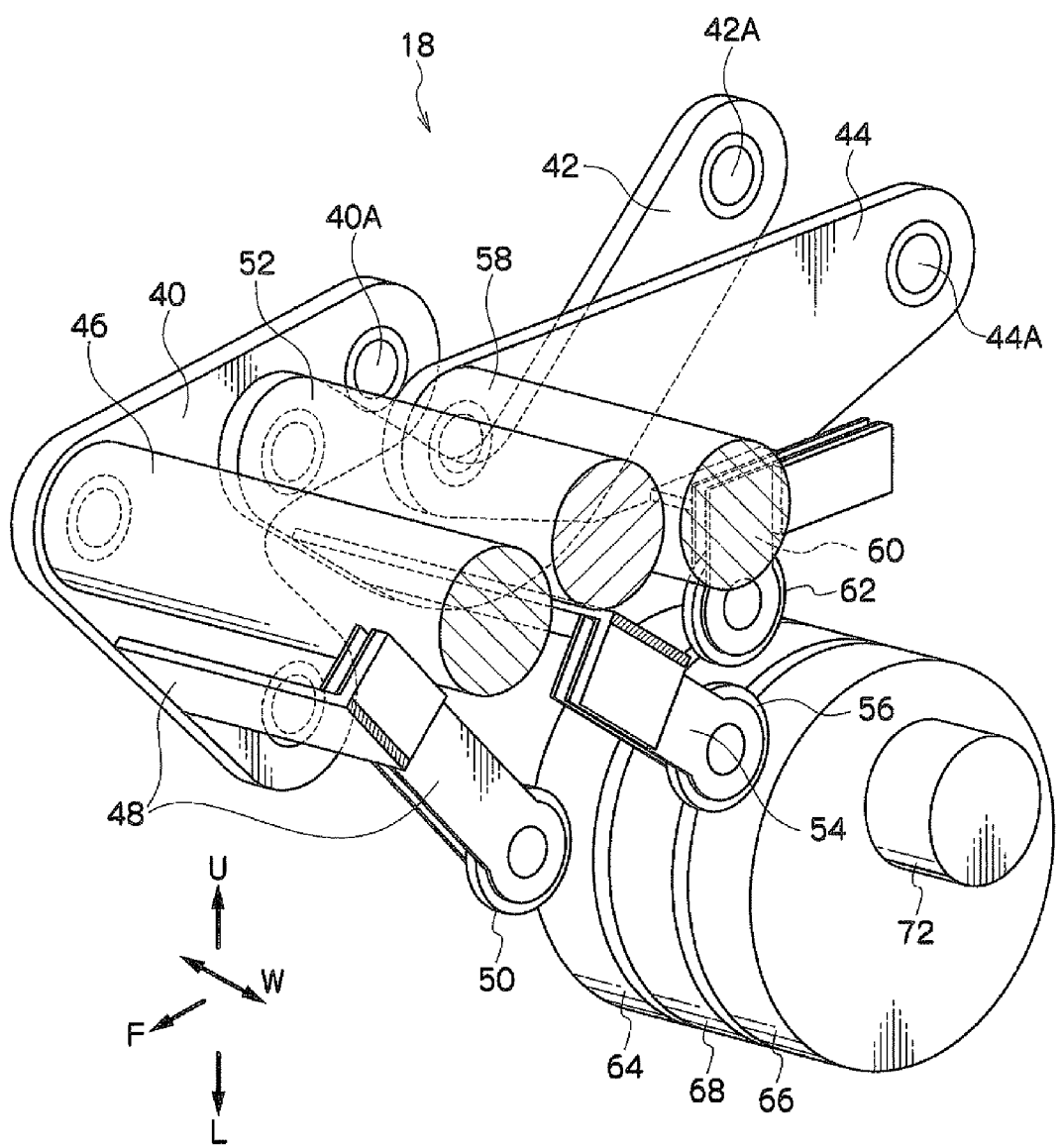
FIG. 8 is a partially cut away perspective view showing a peristalsis mechanism constituting the breast pump relating to the exemplary embodiment of the present invention.

As shown in FIG. 8, the peristalsis mechanism 18 is provided with respective pairs of first arms 40, second arms 42 and third arms 44, which are respectively pivotably supported at a pair of side plates 22C which oppose in the width direction (the direction of arrow W) and constitute the milking side frame 22B. In FIG. 8, the arms at one width direction side are shown and the arms at the other side are not shown. The pair of first arms 40 are formed with the same shape as one another, and pivot 40A are disposed on the same axis as one another. Similarly, the pairs of second arms 42 and third arms 44 are also respectively formed in the same shapes as one another and pivot 42A and pivot 44A are disposed on the same respective axes as one another. The pivot 40A, 42A and 44A are disposed to be separated from one another (at respectively different positions) in this order from the nearer side to a rear side, and are parallel with one another. Further, the first arms 40 and the second arms 42 are respectively disposed at outer sides of the pair of side plates 22C, and the third arms 44 are disposed between the pair of side plates 22C.

As shown in FIG. 8, the pair of first arms 40 are each formed in a substantial letter "V" shape in side view, and the pivot 40A are provided at vicinities of the one end portions. A first stimulation portion 46, which serves as a pressing portion, bridges between the inflection portions of the pair of first arms 40. The first stimulation portion 46 is formed in a substantially cylindrical (roller) shape, the length (axis) direction of which is substantially parallel with the axis of the pivot 40A. One end of a bracket 48 is connected to one of the first arms 40 at the arm portion that is at the opposite side of the turning axis 40A from the first stimulation portion 46. At the other end of the bracket 48, a roller 50 is supported to be pivotable about an axis that is parallel with the pivot 40A. In the peristalsis mechanism 18, the pair of first arms 40 and the bracket 48 are structured such that a triangle joining the respective axes of the pivot 40A, the first stimulation portion 46 and the roller 50 in side view forms an acute triangle.

The pair of second arms 42 are each formed in a substantial symbol "<" shape in side view, and the pivot 42A are provided at one end portion vicinities thereof. A second stimulation portion 52, which serves as a pressing portion, bridges between the other end portions of the pair of second arms 42. The second stimulation portion 52 is formed in a substantially cylindrical shape, the length (axis) direction of which is substantially parallel with the axis of the pivot 42A. One end of a bracket 54 is connected to a middle portion of one of the second arms 42. At the other end of the bracket 54, a roller 56 is supported to be pivotable about an axis that is parallel with the pivot 42A. In the peristalsis mechanism 18, the pair of second awls 42 and the bracket 54 are structured such that a triangle joining the respective axes of the pivot 42A, the second stimulation portion 52 and the roller 56 in side view forms an acute triangle.

The pair of third arms 44 are each formed in a substantial symbol """ shape in side view, and the pivot 44A are provided at one end portion vicinities thereof. A third stimulation portion 58, which serves as a pressing portion, bridges between the other end portions of the pair of third arms 44. The third stimulation portion 58 is formed in a substantially cylindrical shape, the length (axis) direction of which is substantially parallel with the axis of the pivot 44A. One end of a bracket 60 is connected to a vicinity of the inflection portion of one of the third arms 44. At the other end of the bracket 60, a roller 62 is supported to be pivotable about an axis that is parallel with the pivot 44A. In the peristalsis mechanism 18, the pair of third arms 44 and the bracket 60 are structured such that a triangle joining the respective axes of the pivot 44A, the third stimulation portion 58 and the roller 62 in side view forms an acute triangle.

Figure 9:
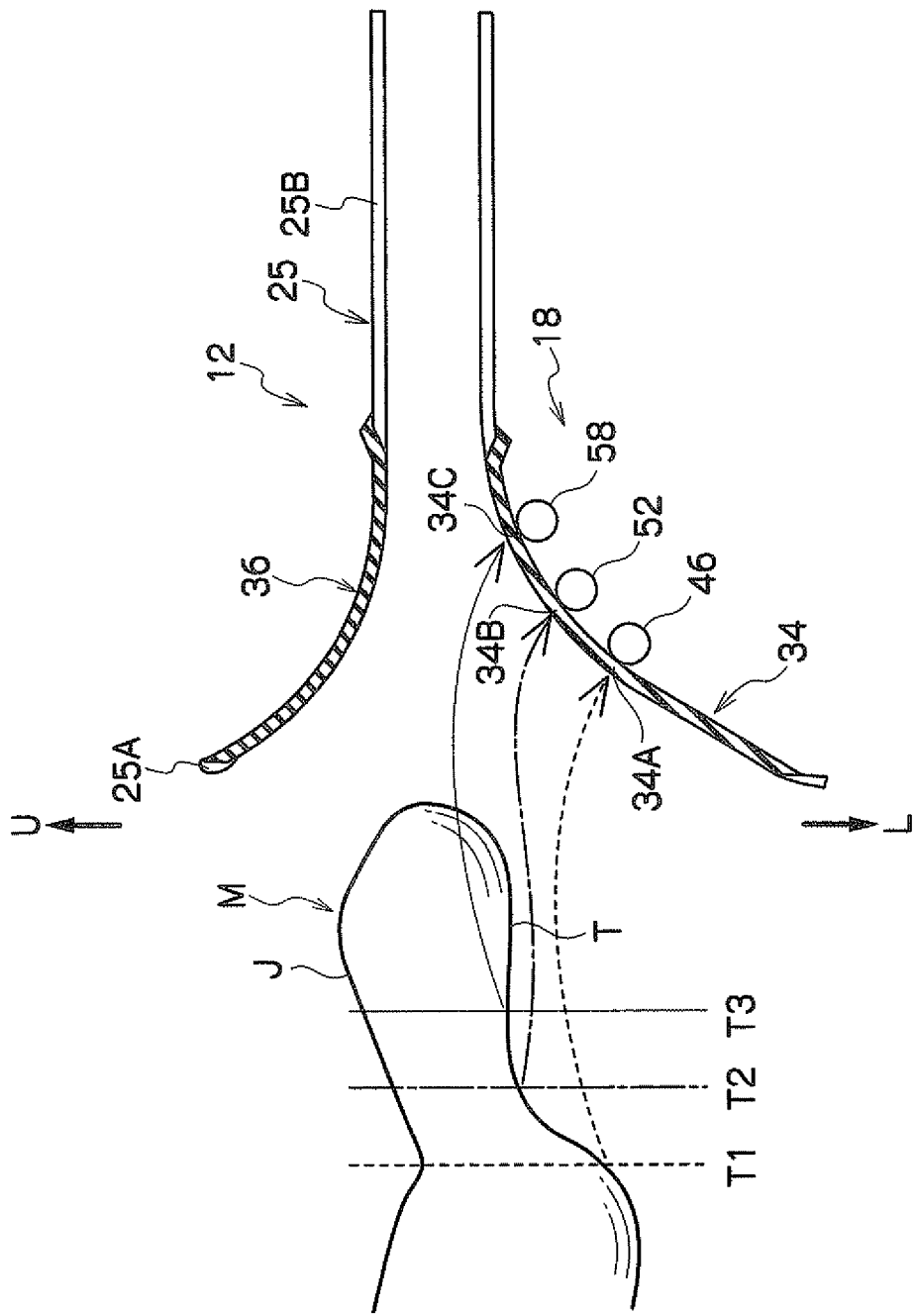
FIG. 9 is a schematic view showing a relationship between peristaltic motion measurement positions in the oral cavity of an infant and locations of expression action by stimulation portions at the pad.

As shown in FIG. 9, the stimulation portions 46, 52 and 58 structuring the peristalsis mechanism 18 are formed so as to press different positions 34A, 34B and 34C of the first flexible portion 34 of the pad 12, each in a substantially normal direction. These positions 34A, 34B and 34C correspond to positions T1, T2, and T3 of a tongue T of an oral cavity M of an infant illustrated in FIG. 9. Here, the reference symbol J indicates an upper jaw portion of the oral cavity M of the infant.

As shown in FIG. 8, the peristalsis mechanism 18 is further provided with cams 64, 66 and 68 against which, respectively, the roller 50 of the first arm 40, the roller 56 of the second arm 42 and the roller 62 of the third arm 44 independently touch. The cams 64, 66 and 68 are respectively formed in substantial disc shapes and are eccentric cams, outer peripheral faces of which are caused to touch against the corresponding rollers 50, 56 and 62. In this exemplary embodiment, the cams 64, 66 and 68 are integrally and pivotably connected to a common rotating shaft 72, which is driven by a common motor 70 (see FIG. 4). The rotating shaft 72 bridges between the pair of side plates 22C and is supported at the milking side frame 22B to be rotatable about its own axis. The motor 70 is retained to be fixed with respect to the milking side frame 22B.

Thus, in the peristalsis mechanism 18, when the motor 70 is operated and the cams 64, 66 and 68 rotate, the first arms 40, the second aims 42 and the third arms 44 turn (rock) about the respective pivot 40A, 42A and 44A, and the first stimulation portion 46, second stimulation portion 52 and third stimulation portion 58 periodically press against the first flexible portion 34 of the pad 12. In this exemplary embodiment, in the peristalsis mechanism 18, the first stimulation portion 46, the second stimulation portion 52 and the third stimulation portion 58 touch the first flexible portion 34 at different positions corresponding to a base side, an intermediate portion and a distal end side of the nipple, and the contact positions are formed so as to press peristaltically in sequence from the base side of the nipple toward the distal end side with predetermined relative differences (a expression action).

Figure 10:
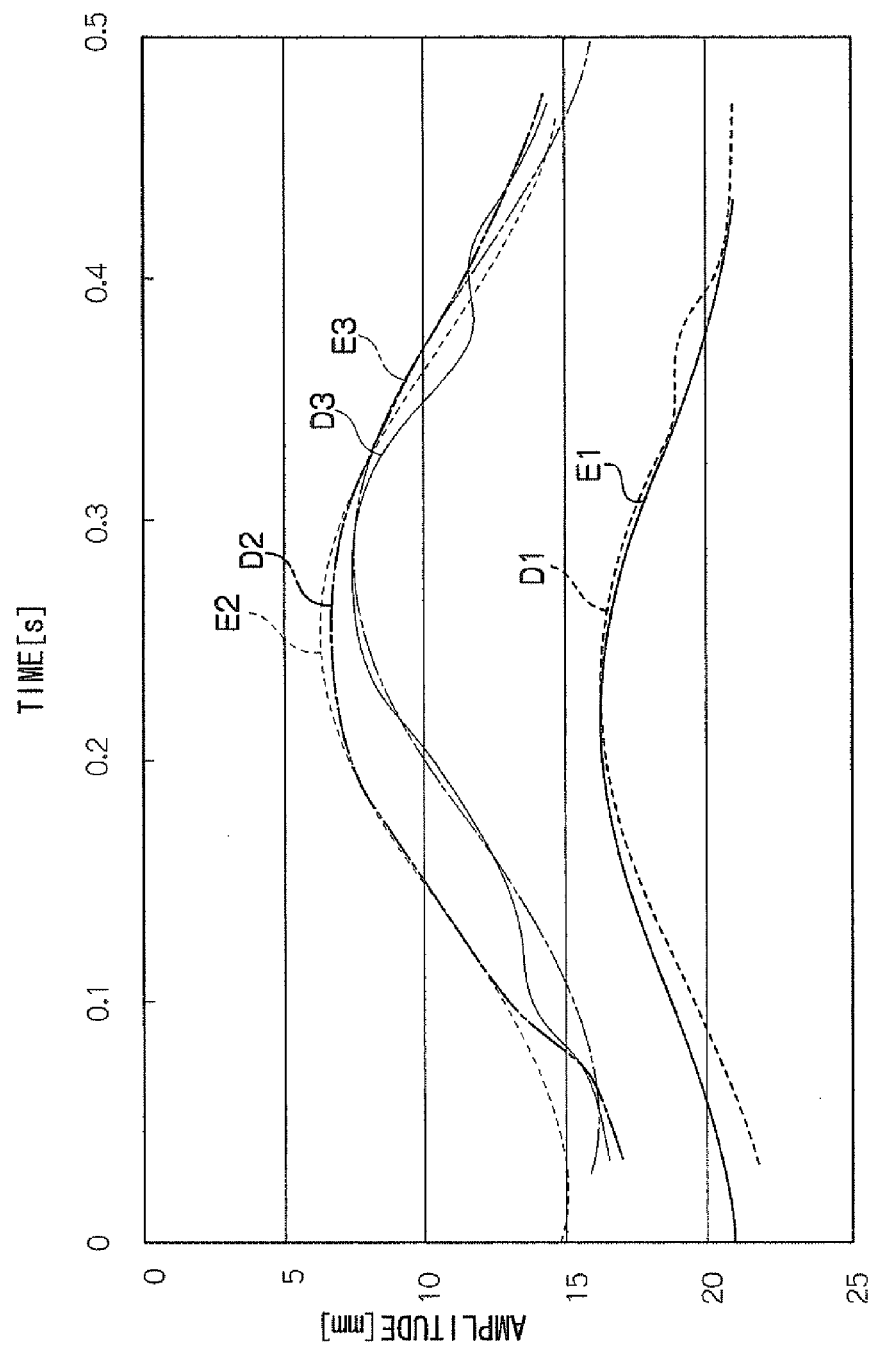
FIG. 10 is a graph showing superposed actions of the stimulation portions of the breast pump relating to the exemplary embodiment of the present invention and curves of peristaltic motion of an infants tongue.

More specifically, as shown in FIG. 10, the first stimulation portion 46, the second stimulation portion 52 and the third stimulation portion 58 are constituted to perform pressing actions on the first flexible portion 34 as are illustrated as pressure curves E1, E2 and E3. Although not described in detail here, in the peristalsis mechanism 18, the dimensions and forms of the portions are determined such that these pressing curves E1, E2 and E3 match curves D1, D2 and D3 that have been measured at the positions T1, T2 and T3, which are separated in the depth direction of the oral cavity M, of the tongue T during actual suckling by an infant. In other words, the peristalsis mechanism 18 is constituted to apply a expression action similar to the peristaltic motion of an infant to the nipple inserted into the pad 12. Here, when the stimulation portions 46, 52 and 58 are pressing the nipple, control is performed to increase generated torque of the motor 70 in accordance with increases in load (for example, control to increase the duty ratio of the motor 70 that is being driven by PWM or the like).

Figure 7:
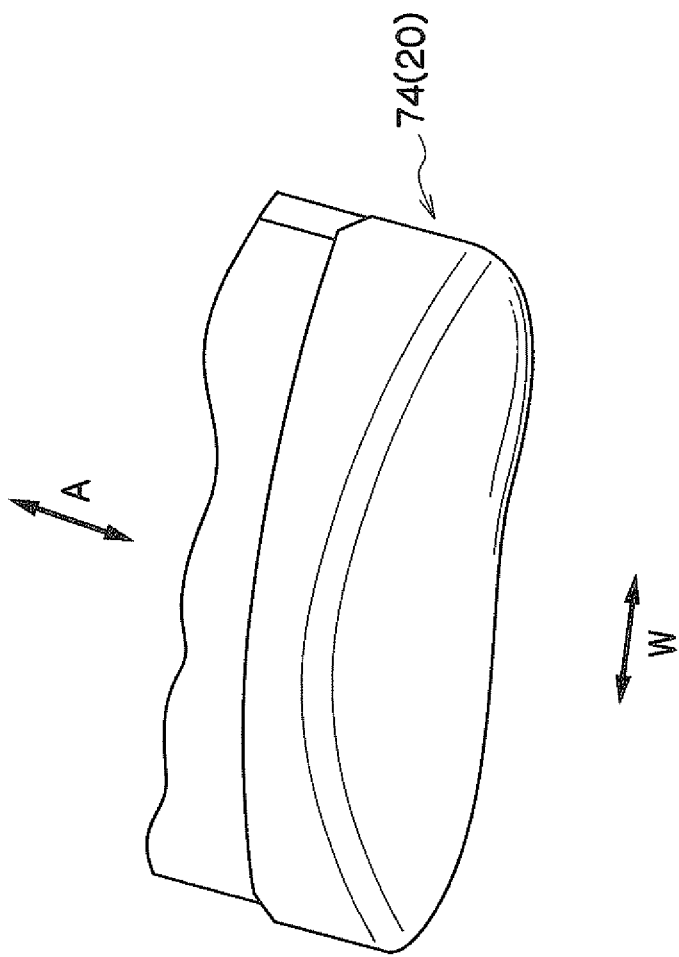
FIG. 7 is a perspective view showing the support piece constituting the breast pump relating to the exemplary embodiment of the present invention.

As shown in FIG. 1 and FIG. 4, the nipple support mechanism 20 includes a support piece 74 which serves as a nipple support member for holding the second flexible portion 36 from the outside of the pad 12. As shown in FIG. 7, the support piece 74 is formed in a block form, which is formed in a substantially elliptical shape whose long axis direction matches the width direction, and of which a central portion in the width (arrow W) direction is recessed relative to the two end portions. The support piece 74 is disposed touching or close to a middle portion of the second flexible portion 36 in the axial direction (between a portion of sharply changing radius and a gently changing portion) of the pad 12, as shown in FIG. 1. The support piece 74 supports the upper side of the nipple to which the actions of the peristalsis mechanism 18 are transmitted.

Figure 5:
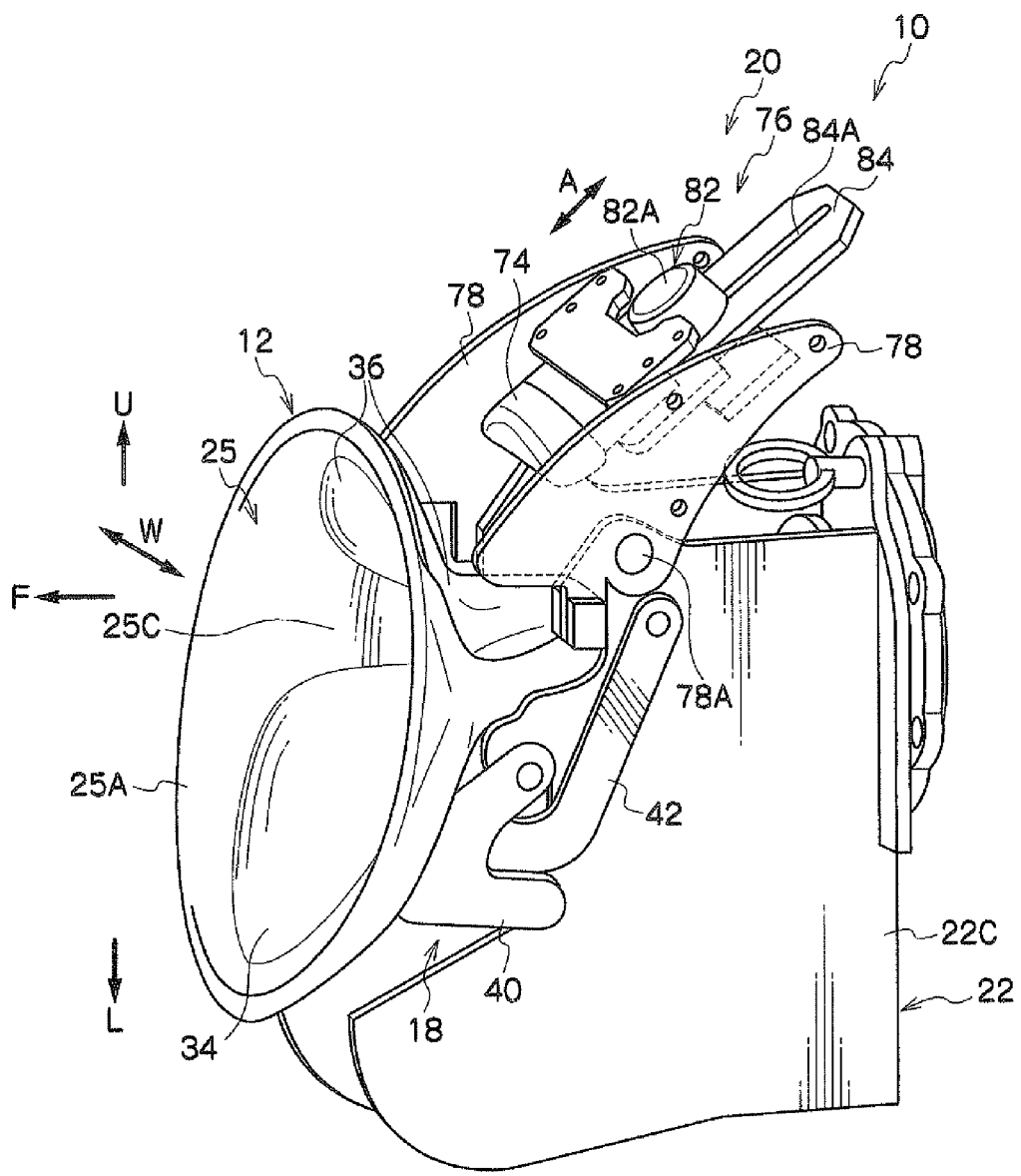
FIG. 5 is a perspective view showing a nipple support mechanism constituting the breast pump relating to the exemplary embodiment of the present invention.

As shown in FIG. 5, a piece position adjusting mechanism 76, which serves as guiding device and retaining device, is disposed at the opposite side of the support piece 74 from the second flexible portion 36 side thereof, The piece position adjusting mechanism 76 is provided with a pair of subframes 78, which are connected or extended to the respective upper sides from the pair of side plates 22C of the device frame 22. A bridging plate 80, which structures the retaining device, bridges between the pair of subframes 78. A stopping screw 82, which functions as a guiding portion and a retaining portion, is screwed with the bridging plate 80.

Further, the piece position adjusting mechanism 76 includes a guided portion 84 that includes a long hole 84A, through which a threaded portion of the stopping screw 82 is passed, and that is disposed between a head portion 82A of the stopping screw 82 and the bridging plate 80. This guided portion 84 is fixedly provided at the opposite side of the support piece 74 from the second flexible portion 36 side thereof. The long hole 84A of the guided portion 84 is formed to be long with length in a direction (the direction of arrow A shown in FIG. 5) in which the support piece 74 is moved toward and away from the second flexible portion 36 (the peristalsis mechanism 18). Thus, the guided portion 84 is constituted with a position thereof being adjustable in a range from a position at which the support piece 74 touches against the second flexible portion 36 of the pad 12 at which no nipple is inserted as shown in FIG. 6A (or a position pushed in to the interior of the pad 12) to a position at which the support piece 74 is greatly separated from the second flexible portion 36 as shown in FIG. 6B.

Thus, in the nipple support mechanism 20, in a state in which the stopping screw 82 of the piece position adjusting mechanism 76 is loosened, the position of the support piece 74 may be adjusted relative to the second flexible portion 36 by the guided portion 84 being slid relative to the bridging plate 80 while being guided by the stopping screw 82 and the long hole 84A. Further, in the nipple support mechanism 20, the position of the guided portion 84 relative to the bridging plate 80, which is to say the position of the support piece 74 relative to the second flexible portion 36, is retained by the stopping screw 82 of the piece position adjusting mechanism 76 being tightened. Turning of the guided portion 84, which is to say the support piece 74, about the stopping screw 82 (a wobbling action) may be restrained by, for example, a guide groove being provided at one of the bridging plate 80 and the guided portion 84 and a guide protrusion that is provided at the other being inserted therein, or by the two width direction ends of the guided portion 84 being made to be close to the pair of subframes 78.

Figure 6A:
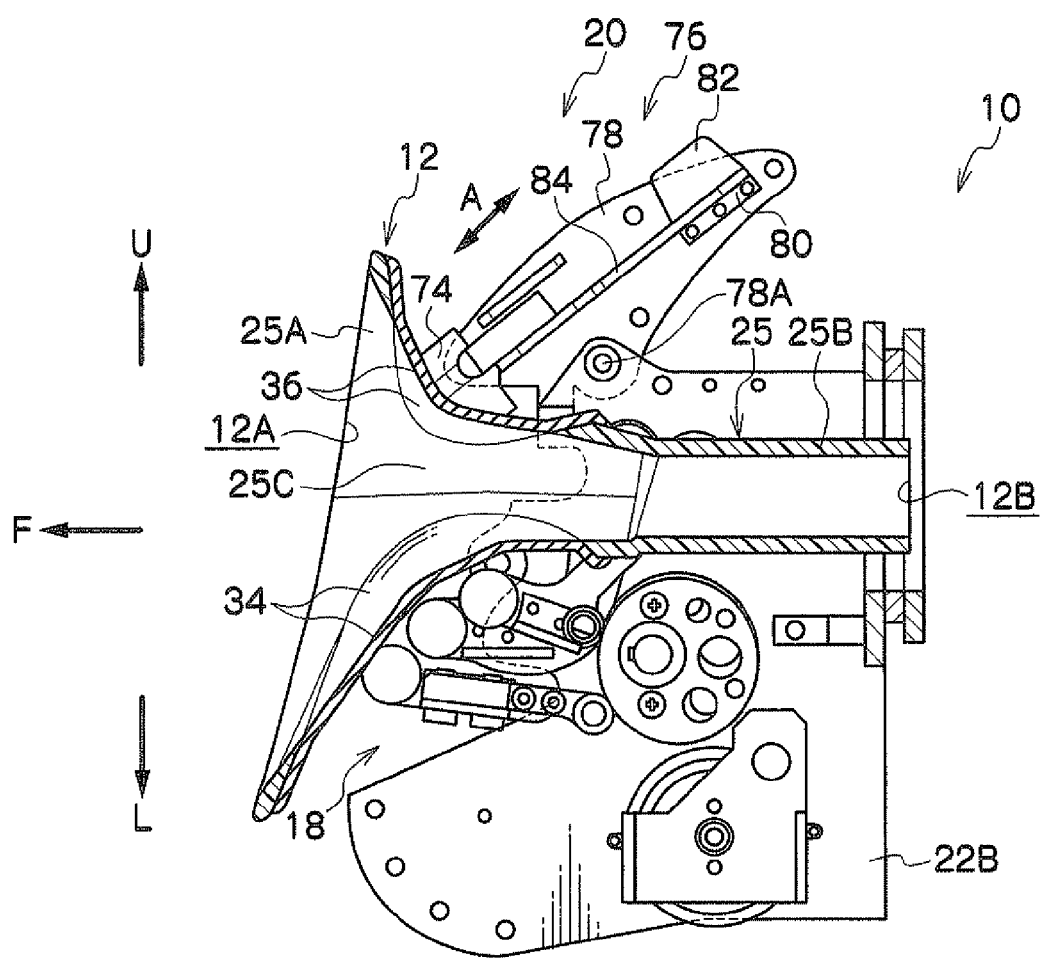
FIG. 6A is a side sectional view showing the nipple support mechanism constituting the breast pump relating to the exemplary embodiment of the present invention, showing a state in which a support piece touches against the pad.
Figure 6B:
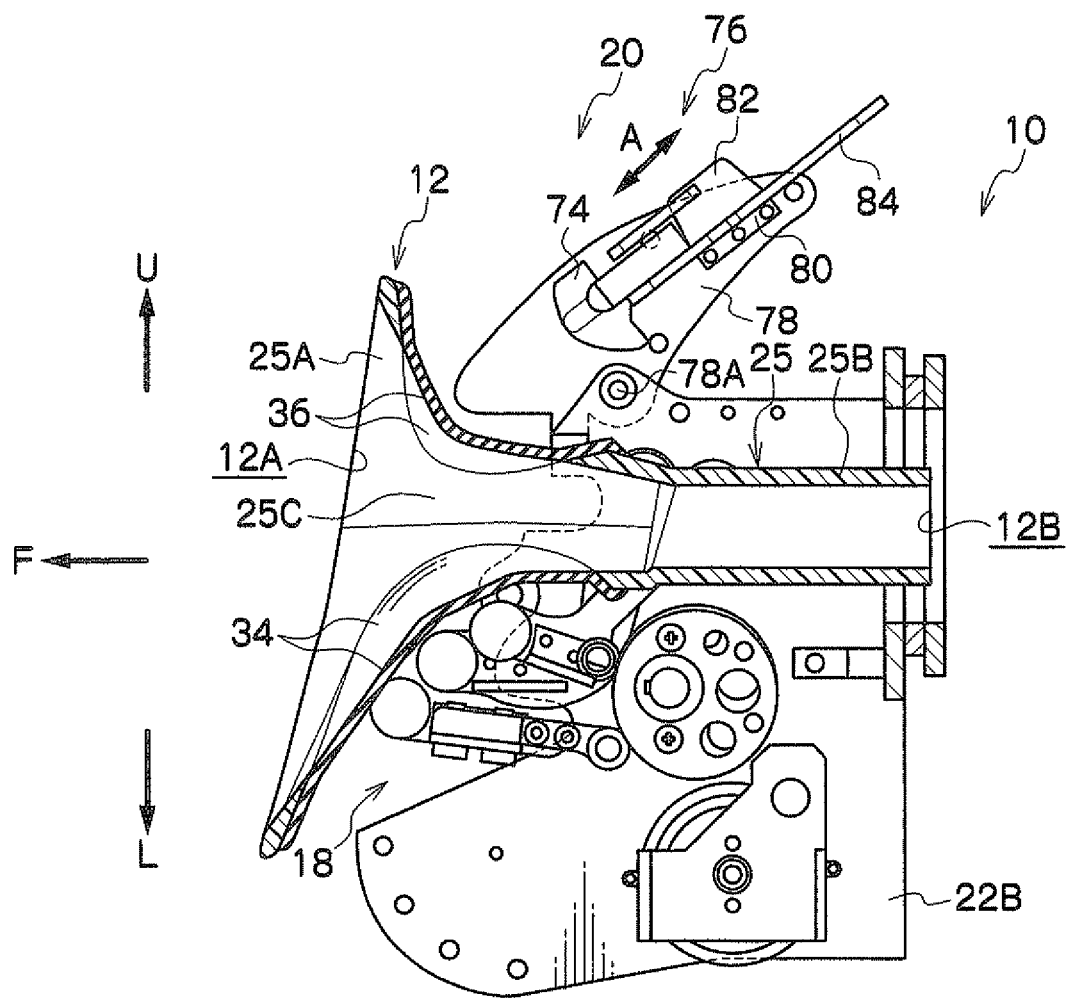
FIG. 6B is a side sectional view showing the nipple support mechanism constituting the breast pump relating to the exemplary embodiment of the present invention, showing a state in which the support piece is moved away from the pad.

Although not illustrated, in this exemplary embodiment the pair of subframes 78 are constituted to be pivotable about a support shaft 78A with respect to the device frame 22, and a constitution is formed in which the support piece 74 may be moved away from the second flexible portion 36 by the pair of the subframes 78 being turned toward the horizontal from a usage position shown in FIG. 6A. Thus, a constitution is formed which may be switched between the usage position and a preparation position (a position for nipple insertion) of the support piece 74, with a state in which the position of the support piece 74 has been adjusted being maintained by the piece position adjusting mechanism 76. A constitution may be formed in which a nipple may be inserted by moving the support piece 74 without turning about the support shaft 78A.

Figure 11A:
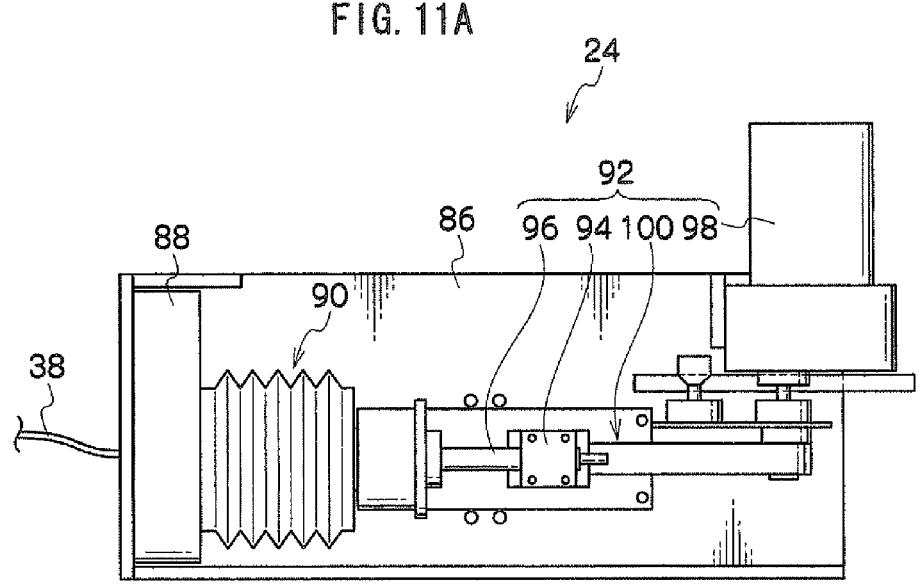
FIG. 11A is a plan view showing a vacuum pump unit constituting the breast pump relating to the exemplary embodiment of the present invention.
Figure 11B:
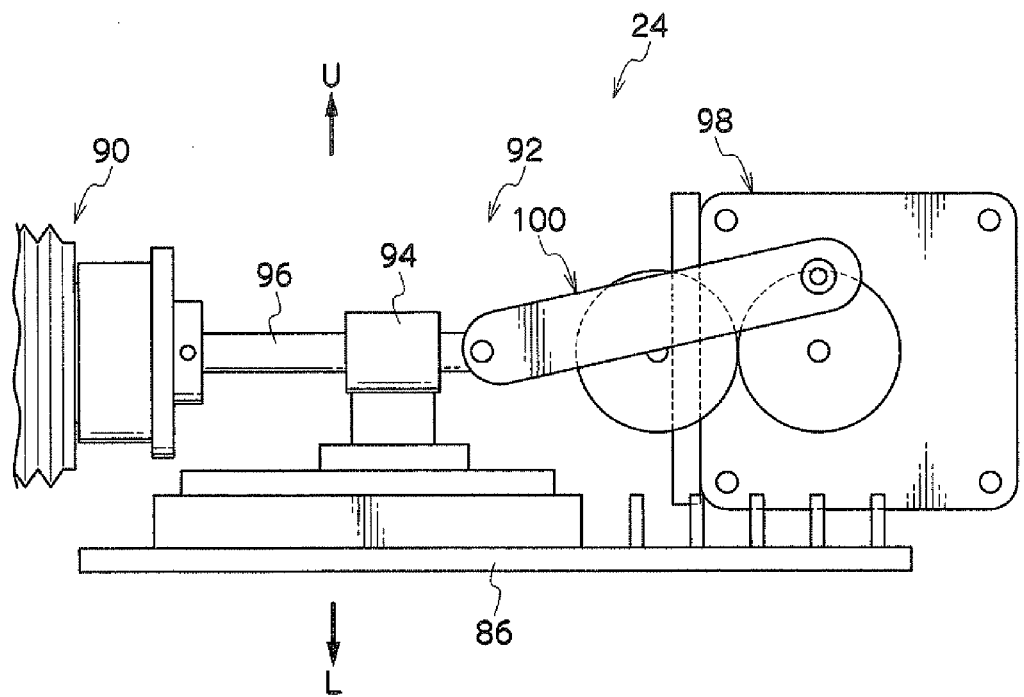
FIG. 11B is a side view showing the vacuum pump unit constituting the breast pump relating to the exemplary embodiment of the present invention.

As shown in FIG. 11A and FIG. 11B, the vacuum pump unit 24 is constituted with, as principal components, a header 88 that is fixed to the unit frame 86 and is connected with the connection pipe 16 via the tube 38, a bellows 90 that is connected with the header 88 at an opening end thereof of the bellows 90, and a driving mechanism 92 that reciprocatingly drives a closed end side of the bellows 90 in an axial direction of the bellows 90. The driving mechanism 92 includes a reciprocating rod 96 that is joined to the closed end of the bellows 90 and is guided in the axial direction of the bellows 90 by a sliding guide 94, and a crank mechanism 100 that converts rotation of a motor 98, which is fixed to the unit frame 86, to a reciprocating action.

This vacuum pump unit 24 is a constitution that applies negative pressure through the connection pipe 16 into the pad 12 at which the nipple entry side opening portion 12A is sealed up by the breast, by expanding and contracting the bellows 90 by the action of the driving mechanism 92. Thus, the vacuum pump unit 24 is a constitution that is at atmospheric pressure at a minimum volume of the bellows 90 and a minimum pressure (negative pressure) at a maximum volume. That is, the vacuum pump unit 24 is a constitution that applies periodically varying negative pressure to the pad 12. The vacuum pump unit 24 is formed such that the driving mechanism 92 is controlled by an unillustrated control device such that the negative pressure applied to the pad 12 varies with a predetermined phase difference with respect to pressure variations (positive pressure) when the nipple is squeezed by the peristalsis mechanism 18. This exemplary embodiment has a constitution in which the driving mechanism 92 is controlled such that the bellows 90 is at the minimum volume when the third stimulation portion 58 of the peristalsis mechanism 18 is disposed at a peak position in the direction of pressing the nipple.

The vacuum pump unit 24 described above is connected to the connection pipe 16 by the flexible tube 38 as shown in FIG. 4, and is placed on a table or the like and operated. Alternatively, although not illustrated, a milking unit 102 which includes the pad 12, the nursing bottle 14, the connection pipe 16, the peristalsis mechanism 18, the nipple support mechanism 20 and the device frame 22, operates in a state in which the milking unit 102 is held by a user (the subject of milking).

Next operation of the exemplary embodiment will be described.

When milking is to be performed by the breast pump 10 with the constitution described above, firstly, the pair of subframes 78 are turned about the support shaft 78A, and in the state in which the support piece 74 of the nipple support mechanism 20 has been moved away from the second flexible portion 36 of the pad 12, the milking unit 102 including the pad 12 is brought close to a breast such that the nipple is inserted into the pad 12 (principally the constricting-form portion 25A of the tubular frame 25) through the nipple entry side opening portion 12A, and the nipple entry side opening portion 12A of the pad 12 is pressed against the breast.

Then, the subframes 78 are returned, the stopping screw 82 is loosened, the guided portion 84 is slid relative to the bridging plate 80, the support piece 74 is caused to touch against the second flexible portion 36 of the pad 12 in the state in which the nipple is inserted, and the stopping screw 82 is tightened. If the position of the support piece 74 has been specified beforehand, the nipple may be inserted into the pad 12 at a standard position with the subframes 78 of the nipple support mechanism 20 dropped toward the horizontal, and then the subframes 78 may be set to the usage position.

Then, the peristalsis mechanism 18 and the vacuum pump unit 24 are operated together. Accordingly, the pairs of first arms 40, second arms 42 and third arms 44 of the peristalsis mechanism 18 are driven and rocked by the corresponding cams 64, 66 and 68, and the stimulation portions 46, 52 and 58 respectively transmit a expression action to the nipple via the first flexible portion 34. Thus, the nipple is directly stroked with a peristaltic motion that reproduces a peristaltic motion by the tongue of an infant. At this time, the nipple is supported from the opposite side thereof from the peristalsis mechanism 18 (the upper side) by the support piece 74 of the nipple support mechanism 20 via the second window portion 28. Further, inside the pad 12 which is sealed up by the nipple being inserted, negative pressure is periodically applied by the action of the vacuum pump unit 24 with a predetermined phase difference from the pressure (positive pressure) variations caused by the peristaltic motion, and breast milk entering into the pad 12 is gathered.

Because of the application of positive pressure by the peristalsis mechanism 18 (the peristaltic motion) and the application of negative pressure by the vacuum pump unit 24, milking may be carried out in conditions close to a milking motion by an infant. The gathered breast milk passes from the pad 12 through the connection pipe 16, flows into the nursing bottle 14, and is collected in the nursing bottle 14.

Now, in the present breast pump 10, because the first flexible portion 34 and the second flexible portion 36 are provided at the tubular frame 25, the peristaltic motion of the peristalsis mechanism 18 may be transmitted from the first flexible portion 34 to the nipple in the pad 12 while deformations of the pad 12 as a whole are suppressed by the tubular frame 25, and surface contact between the nipple (the breast) and the pad 12 is assured by the second flexible portion 36. Therefore, in the breast pump 10 which applies positive pressure (the peristaltic motion) to the nipple in the pad 12 with the peristalsis mechanism 18 and negative pressure with the vacuum pump unit 24, the formation of gaps between the pad 12 and the breast in association with the milking action is prevented. That is, the pad 12 is employed in the breast pump 10 and breast milk may be gathered effectively.

Further, in the breast pump 10, because the nipple in the pad 12 is supported from the opposite side thereof from the peristalsis mechanism 18 by the nipple support mechanism 20 from the outside of the pad 12, the peristaltic motion by the peristalsis mechanism 18 may be reliably transmitted to the nipple in the pad 12. Moreover, because the portion of the pad 12 that the support piece 74 of the nipple support mechanism 20 touches is the second flexible portion 36, the second flexible portion 36 deforms in accordance with the shape of the nipple inserted into the pad 12. Thus, a constitution is realized in which the position of support of the nipple by the nipple support mechanism 20 (the space between the support piece 74 and the peristalsis mechanism 18), which is to say the position of abutting of the nipple against the support piece 74 via the second flexible portion 36, may be adjusted.

Thus, the breast pump 10 in which the pad 12 is employed may both prevent deformations of the pad 12 (the formation of gaps between the pad 12 and the breast) in association with milking actions as described above and implement adjustments of the nipple support position in accordance with variations in nipple shape, personal differences and the like. In the breast pump 10, the function of adjustment of the nipple support position is realized by the provision of the piece position adjusting mechanism 76 at the nipple support mechanism 20. Further, because the piece position adjusting mechanism 76 is constituted to include the guiding device (principally the long hole 84A of the guided portion 84 and the stopping screw 82) that guides the support piece 74 in the direction toward and away from the second flexible portion 36 and the retaining device (principally the bridging plate 80 and the stopping screw 82) capable of retaining the support piece 74 (the guided portion 84) at the bridging plate 80 (the pad 12) at an arbitrary position, the task of adjustment of the nipple support position with the support piece 74 is simple.

In the exemplary embodiment described above, an example in which the pad 12 employed in the breast pump 10 includes the second flexible portion 36 has been illustrated, but the present invention is not limited thus. For example, a constitution may be formed in which the nipple in the pad 12 is supported by a support piece 74 through which the constricting-form portion 25A passes in a sealed condition.

Further, in the exemplary embodiment described above, an example is illustrated in which the support position of the nipple in the pad 12 is adjusted by the support piece 74 moving toward or away from the second flexible portion 36, but the present invention is not limited thus. For example, a constitution may be formed in which the second flexible portion 36 is formed in a balloon form and the support position of the nipple in the pad 12 is adjusted by air amounts that flow therein, and a constitution may be formed in which the support position of the nipple in the pad 12 is adjusted by padding between the second flexible portion 36 and the nipple or between the outer side of the second flexible portion 36 and a fixed portion.

EXPLANATION OF REFERENCE NUMERALS

10 Breast pump
12 Pad (nipple covering member)
12A Nipple entry side opening portion
12B Connection side opening portion
14 Nursing bottle (collection vessel)

18 Peristalsis mechanism (stimulating device)
20 Nipple support mechanism (nipple support portion and support position adjusting device)
24 Vacuum pump unit (negative pressure generating device)
25 Tubular frame
25B Straight pipe portion
26 First window portion (first window portion)
28 Second window portion (second window portion)
32 Silicone rubber (elastic member)
34 First flexible portion (first flexible portion)
36 Second flexible portion (second flexible portion)
74 Support piece (nipple support member)
76 Piece position adjusting mechanism (guiding device, retaining device)

The invention claimed is:

1. A breast pump comprising:
a nipple covering member with a tubular frame at which a large diameter side opening for inserting a nipple is formed at one end side and a small diameter side opening is formed at the other end side,
a first flexible portion that is provided on a surface area of the nipple covering member between the large diameter side opening and the small diameter side opening of the tubular frame and that can be deformed inward of the tubular frame by a pressing force from an outside of the tubular frame, and
a second flexible portion that is provided on the surface area of the nipple covering member and that is separated from the first flexible portion by an element in the tubular frame, wherein the second flexible portion is provided at a position opposing the first flexible portion between the large diameter side opening and the small diameter side opening of the tubular frame and that can be deformed outward of the tubular frame by a pressing force from an inside of the tubular frame;
a collection vessel for collecting milk, which is connected to the small diameter side opening of the nipple covering member;
a stimulating device for transmitting pressing stimulations to the nipple at the first flexible portion; and
a nipple support mechanism having a nipple support portion and a support adjusting device, wherein the support adjusting device contacts the nipple support portion and is configured to move the nipple support portion; wherein:
  (i) the nipple support portion supports the nipple inserted into the nipple covering member with respect to the pressing stimulations by the stimulating device on the nipple that are transmitted via the first flexible portion, the nipple support portion being disposed at the outside of the second flexible portion of the nipple covering member,
  (ii) the nipple support portion comprises a nipple support member configured to be movable along an axial direction of the tubular frame between the first position that contacts the second flexible portion of the nipple covering member and the second position in which no portion of the nipple support portion contacts the second flexible portion of the nipple covering member, and
  the support position adjusting device is capable of moving the support position of the nipple support portion relative to the stimulating device, and is capable of moving the nipple support portion to have at least two positions, a first position in which a portion of the nipple support portion contacts the second flexible portion of the nipple covering member and a second position in which no portion of the nipple support portion contacts the second flexible portion of the nipple covering member, wherein the support position adjusting device comprises:
    (a) a guiding device that guides the nipple support member to move toward and away from the stimulating device, wherein the guiding device comprises a slot extending a length of the guiding device for receiving a retaining member; and
    (b) the retaining member capable of retaining the nipple support member at a plurality of positions along the slot of the guiding device in the toward/away direction with respect to the stimulating device, wherein the retaining member comprises a stopping screw.

2. The breast pump according to claim 1, further comprising a negative pressure generating device for producing negative pressure at the inside of the nipple covering member into which the nipple has been inserted through the large diameter side opening.

3. The breast pump according to claim 1, wherein the first and the second flexible portions have a lower stiffness than the element in the tubular frame.

4. A breast pump comprising:
a nipple covering member with a tubular frame at which a large diameter side opening for inserting a nipple is formed at one end side and a small diameter side opening is formed at the other end side,
a first flexible portion that is provided on a surface area of the nipple covering member between the large diameter side opening and the small diameter side opening of the tubular frame and that can be deformed inward of the tubular frame by a pressing force from an outside of the tubular frame, and
a second flexible portion that is provided on the surface area of the nipple covering member and that is separated from the first flexible portion by an element in the tubular frame, wherein the second flexible portion is provided at a position opposing the first flexible portion between the large diameter side opening and the small diameter side opening of the tubular frame and that can be deformed outward of the tubular frame by a pressing force from an inside of the tubular frame, the tubular frame including a first window portion, which is formed at a circumferential direction portion between the large diameter side opening and the small diameter side opening, and a second window portion, which is formed such that skeleton portions are formed between the second window portion and two circumferential direction end portions of the first window portion, the first flexible portion comprising the first window portion being closed up by an elastic member, and the second flexible portion comprising the second window portion being closed up by another elastic member;
a collection vessel for collecting milk, which is connected to the small diameter side opening of the nipple covering member;
a stimulating device for transmitting pressing stimulations to the nipple at the first flexible portion; and
a nipple support mechanism having a nipple support portion and a support adjusting device; wherein the support adjusting device contacts the nipple support portion and is configured to move the nipple support portion; wherein:
  (i) the nipple support portion supports the nipple inserted into the nipple covering member with respect to the pressing stimulations by the stimulating device on the nipple that are transmitted via the first flexible portion, the nipple support portion being disposed at the outside of the second flexible portion of the nipple covering member, ii) the nipple support portion comprises a nipple support member configured to be movable along an axial direction of the tubular frame between the first position that contacts the second flexible portion of the nipple covering member and the second position in which no portion of the nipple support portion contacts the second flexible portion of the nipple covering member, and the support position adjusting device is capable of moving the support position of the nipple support portion relative to the stimulating device, and is capable of moving the nipple support portion to have at least two positions, a first position in which a portion of the nipple support portion contacts the second flexible portion of the nipple covering member and a second position in which no portion of the nipple support portion contacts the second flexible portion of the nipple covering member, wherein the support position adjusting device comprises:

(a) a guiding device that guides the nipple support member to move toward and away from the stimulating device, wherein the guiding device comprises an slot extending a length of the guiding device for receiving a retaining member; and (b) the retaining member capable of retaining the nipple support member at a plurality of positions along the slot of the guiding device in the toward/away direction with respect to the stimulating device, wherein the retaining member comprises a stopping screw.

5. The breast pump according to claim 4, further comprising a negative pressure generating device for producing negative pressure at the inside of the nipple covering member into which the nipple has been inserted through the large diameter side opening.

* * * * *